United States Patent [19]

Weber et al.

[11] 4,307,252

[45] Dec. 22, 1981

[54] 2-PROPYL-PENT-4-EN-1-AL

[75] Inventors: Jürgen Weber, Oberhausen; Wolfgang Bernhagen, Mülheim; Helmut Springer, Oberhausen, all of Fed. Rep. of Germany

[73] Assignee: Ruhrchemie Aktiengesellschaft, Oberhausen, Fed. Rep. of Germany

[21] Appl. No.: 173,792

[22] Filed: Jul. 30, 1980

Related U.S. Application Data

[62] Division of Ser. No. 83,893, Oct. 11, 1979.

[30] Foreign Application Priority Data

Oct. 13, 1978 [DE] Fed. Rep. of Germany ....... 2844635

[51] Int. Cl.³ .................. C07C 45/51; C07C 47/21
[52] U.S. Cl. .................................................. 568/450
[58] Field of Search ............................ 568/450, 448

[56] References Cited

U.S. PATENT DOCUMENTS 4,071,563  1/1978  Kummer et al. .................... 568/450
4,107,217  8/1978  Schreiber et al. .................. 568/450

Primary Examiner—Werren B. Lone
Attorney, Agent, or Firm—Sprung, Felfe, Horn, Lynch & Kramer

[57] ABSTRACT

2-Propyl-pent-4-en-1-al of the formula

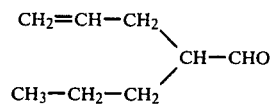

and a process for its preparation.

2 Claims, No Drawings

2-PROPYL-PENT-4-EN-1-AL

This is a division of application Ser. No. 83,893 filed Oct. 11, 1979.

BACKGROUND OF THE INVENTION

1. Field of the Invention

This invention relates to the unsaturated aldehyde 2-propyl-pent-4-en-1-al of the formula

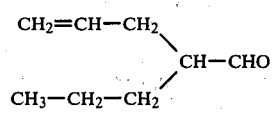

and a process for preparing the same.

2. Discussion of the Prior Art

Pent-4-en-1-al and various substitution products of this unsaturated aldehyde are known from the literature. German Auslegeschrift 25 17 447 describes the preparation of pent-4-en-1-al from an acetaldehyde acetal containing at least one allyl alcohol radical. In accordance with the known procedure, the acetal is passed at 350° to 450° C. in the gaseous phase over a surface-active catalyst. Under the reaction conditions a mol of allyl alcohol splits off, and the doubly unsaturated ether thereby formed rearranges to pent-4-en-1-al.

The preparation of substituted pent-4-en-1-als is the subject of a publication by Kent C. Brannock in J. Am. Chem. Soc. 81 (1959), 3382. Aldehyde diallylacetals are used as starting materials, from which one mol of allyl alcohol is split off under the catalytic effect of acid. Allyl alkenyl ethers are formed, which can rearrange to form the substituted 4-pentenals without previously having been isolated.

SUMMARY OF THE INVENTION 2-propyl-pent-4-en-1-al, a compound that has not hitherto been described in the literature, is an odoriferous substance having a fragrance that differs from other odoriferous substances available on the market. It can also be used as an intermediate product in the preparation of other organic compounds, e.g., 2,2-dipropylethanol, 2,2-dipropylethylamine, 2-propyl-valeraldehyde, 2-propyl-hexane-1,6-dial. 2-propyl-pent-4-en-1-al boils at 161° C.

The preparation of 2-propyl-pent-4-en-1-al is carried out in accordance with the invention from n-valeraldehyde, which is reacted with at least 2 mols of allyl alcohol to form the corresponding diacetal. The acetal formation is preferably carried out in a solvent, e.g., cyclohexane, n-hexane, n-hexene and in the presence of an acid catalyst, e.g., p-toluenesulfonic acid.

$$CH_3-CH_2-CH_2-CH_2-CHO + 2\ CH_2=CH-CH_2OH \longrightarrow$$

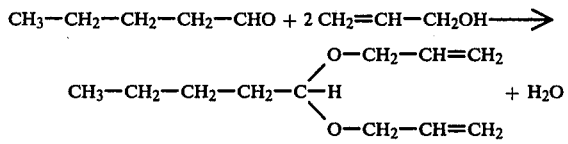

The crude acetal is then distilled and thermally split, allyl-1-pentenyl-ether being formed according to the following reaction equation:

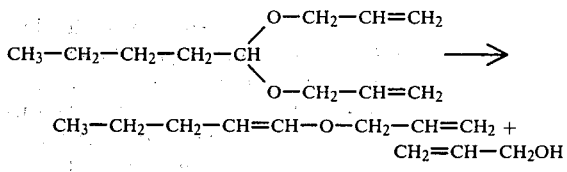

$$CH_3-CH_2-CH_2-CH=CH-O-CH_2-CH=CH_2 + CH_2=CH-CH_2OH$$

The unsaturated ether is finally thermally rearranged to form the compound of the invention.

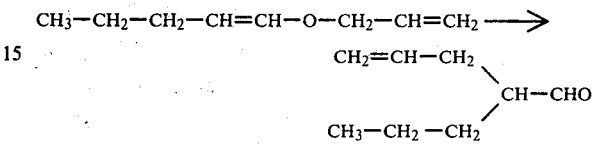

The splitting of the acetal and rearrangement can take place at least to some extent side-by-side. This has the result that the distillation product of the crude acetal contains not only the unsaturated ether, but also the end produce, i.e., the unsaturated aldehyde.

Compared with the known processes for preparing pent-4-en-1-al and the substituted pentenals, the new procedure has the advantage that the 2-propyl-pent-4-en-1-als can be prepared in high yield in a non-catalytic, purely thermal process.

The 2-propyl-pent-4-en-1-al, prepared in accordance with this invention, can be converted to 2,2-dipropylethanol, which is useful as an intermediate for the preparation of 2-propylpentanoic acid (2.2-di-n-propyl-acetic acid), which is used for the synthesis of agents to treat epilepsy, prepared by the hydrogenation of the unsaturated 2-propyl-pent-4-en-1-al using Ni catalysts.

It can be converted to 2,2-dipropylethylamine, useful as an additive for lubricants and corrosion-inhibitors, prepared by well known reductive amination of the unsaturated 2-propyl-pent-4-en-1-al, or it can be converted to 2-propyl-valeraldehyde, useful as an intermediate for the preparation of 5.5-di-n-propylbarbituric acid, prepared by partial hydrogenation of the unsaturated 2-propyl-pent-4-en-1-al in the presence of palladium catalysts.

In accordance with the process of this invention, the 2-propyl-pent-4-en-1-al is prepared by the thermal treatment of valeraldehyde-diallylacetal. This thermal treatment is preferably conducted at a temperature between 150° and 200° C., for between 2 and 30 minutes. The thermal treatment is preferably conducted at subatmospheric pressure. As a result of this thermal treatment, performed optionally in the presence of a catalyst, there is formed crude allyl-1-pentenylether from which the 2-propyl-pent-4-en-1-al is formed. This latter compound is formed by rearrangement of the allyl-1-pentenylether by subjecting the allyl-1-pentenylether to a temperature of 250° to 350° C., optionally in the absence of a catalyst. Preferably, the allyl-1-pentenylether is heated for a period of time between 5 and 30 seconds at 250° to 350° C. While both sub- and superatmospheric pressures can be employed, the process is desirably carried out, for reasons of economy, at atmospheric pressure.

In order to more fully illustrate the nature of the invention and the manner of practicing the same, the following example is presented:

EXAMPLE 1160 g of allyl alcohol (20 mols), 860 g of n-valeraldehyde (10 mols), 1200 g of n-hexane and 1 g of p-toluenesulfonic acid are heated under reflux in a 6 liter volume round-bottomed flask provided with a stirrer, internal thermometer, reflux condenser and water separator. The reaction water formed is continuously removed from the system via the water separator. After six hours, the sump temperature reaches a maximum of 77° C., at which point the reaction is stopped. The yield of n-pentenal-diallyl acetal is about 72 percent of theory.

The crude acetal is distilled in a 1 meter column with 24 theoretical trays in such a way that most of the n-hexane passes over initially as a first fraction at a head temperature of 66° C. and a sump temperature of 120° C. (at normal pressure). A head temperature of 145° C. and a sump temperature of 182° C. are then established at a pressure of 100 mm Hg.

Under these reaction conditions, the full acetal is almost quantitatively split, the doubly unsaturated allyl 1-pentenyl ether being principally formed, which partially reacts further to form 2-propyl-pent-4-en-1-al. The second fraction has the following composition as determined by gas chromatography:

2.1 percent n-hexane
6.1 percent n-valeraldehyde
30.6 percent allyl alcohol
44.2 percent allyl 1-pentenylether
11.7 percent isomeric ethers
5.3 percent 2-propyl-pent-4-en-1-al The yield, calculated as the total of allyl 1-pentenyl ether, isomeric ethers and 2-propyl-pent-4-en-1-al, is about 69 percent of theory, relative to the n-valeraldehyde used, or about 96 percent of theory relative to the full acetal used.

The second fraction obtained as described above is thermally treated in an electrically heated tube provided with a high efficiency cooler and a collection flask. The tube is fulled with Raschig rings of size 5×4 mm; the tube volume is 380 ml. By means of a metering pump, 570 ml of liquid per hour, corresponding to a space velocity of 1.5, are added to the tube per hour at 300° C.

1375 g of crude 2-propyl-pent-4-en-1-al are obtained from 1410 g of crude allyl 1-pentenylether.

821 g, corresponding to a yield of 95 percent, of a 99.5 percent pure 2-propyl-pent-4-en-1-al are obtained by fractional distillation, corresponding to a total yield of 65 percent relative to the n-valeraldehyde used. The yield can be still further substantially improved by reusing unreacted starting materials.

What is claimed is:

1. A process for preparing 2-propyl-pent-4-en-1-al which comprises subjecting valeraldehyde-diallylacetal to a temperature in the range of 120° to 190° C., and rearranging the unsaturated ether so formed at 250° to 350° C.

2. A process according to claim 1 wherein the process is carried out in the absence of a catalyst.

* * * * *